(12) United States Patent
Childers

(10) Patent No.: US 7,707,964 B2
(45) Date of Patent: May 4, 2010

(54) PHARMACEUTICAL DISPENSING APPARATUS AND METHOD

(75) Inventor: Winthrop D. Childers, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 11/361,438

(22) Filed: Feb. 24, 2006

(65) Prior Publication Data

US 2007/0056511 A1    Mar. 15, 2007

Related U.S. Application Data

(60) Continuation of application No. 10/625,813, filed on Jul. 22, 2003, now abandoned, which is a division of application No. 09/877,896, filed on Jun. 7, 2001, now Pat. No. 6,623,785.

(51) Int. Cl.
*B05C 11/10* (2006.01)
*B41J 29/38* (2006.01)

(52) U.S. Cl. .................. 118/695; 118/696; 118/313; 118/317; 347/14; 347/55

(58) Field of Classification Search .............. 427/2.21, 427/2.14, 2.31, 258, 261, 402, 427.2, 201, 427/2.1, 31; 118/695, 696, 313, 317; 239/102.1, 239/102.2; 347/55, 14
See application file for complete search history.

(56) References Cited

U.S. PATENT DOCUMENTS

| | | |
|---|---|---|
| 4,322,449 A | 3/1982 | Voss et al. |
| 4,384,960 A | 5/1983 | Polley |
| 4,548,825 A | 10/1985 | Voss et al. |
| 4,967,208 A | 10/1990 | Childers |
| 5,077,565 A * | 12/1991 | Shibaike et al. ............... 347/15 |
| 5,278,584 A | 1/1994 | Keefe et al. |
| 5,284,133 A | 2/1994 | Burns et al. |
| 5,609,908 A | 3/1997 | Voss |
| 5,819,816 A | 10/1998 | Mayer |
| 5,874,974 A | 2/1999 | Courian et al. |
| 5,881,716 A | 3/1999 | Wirch et al. |
| 5,894,841 A | 4/1999 | Voges |
| 5,925,732 A | 7/1999 | Ecker et al. |
| 5,992,742 A | 11/1999 | Sullivan et al. |
| 6,039,430 A | 3/2000 | Helterline et al. |
| 6,061,608 A | 5/2000 | Moldavsky |
| 6,086,942 A | 7/2000 | Carden, Jr. et al. |
| 6,097,993 A | 8/2000 | Skupin et al. |

(Continued)

FOREIGN PATENT DOCUMENTS

DE    19940241    8/1999

(Continued)

*Primary Examiner*—George R Koch, III

(57) ABSTRACT

An apparatus and method for manufacturing a pharmaceutical dose which dispenses a variable selectable quantity of at least one pharmaceutical onto a pharmaceutical receiving medium. The quantity of the dispensed pharmaceutical(s) are controllably dispensed to customize each pharmaceutical dose to suit the needs of a particular user. The apparatus is coupled by an external telecommunication network to a remote signal source for receiving pharmaceutical quantity and type data for custom manufacturing a pharmaceutical dose. In one aspect, a replaceable cartridge contains a reservoir carrying at least one pharmaceutical component and a fluid drop generator which is mountable in the fluid dispenser. The reservoir may contain a number of separate compartments, each carrying different pharmaceutical component.

16 Claims, 2 Drawing Sheets

U.S. PATENT DOCUMENTS

| | | | |
|---|---|---|---|
| 6,143,353 A | 11/2000 | Oshlack et al. | |
| 6,196,663 B1 | 3/2001 | Wetchler et al. | |
| 6,281,145 B1 * | 8/2001 | Deguchi et al. | 438/782 |
| 6,294,020 B1 * | 9/2001 | Luthje et al. | 118/218 |

FOREIGN PATENT DOCUMENTS

| | | |
|---|---|---|
| FR | 2679516 | 7/1991 |
| WO | WO 98/36739 | 8/1998 |
| WO | WO 00/25754 | 5/2000 |

* cited by examiner

PHARMACEUTICAL DISPENSING APPARATUS AND METHOD

CROSS REFERENCE TO RELATED APPLICATIONS

This application is a continuation of U.S. Ser. No. 10/625,813 filed on Jul. 22, 2003, now abandoned, which itself is a divisional of U.S. Ser. No. 09/877,896 filed on Jun. 7, 2001, issued as U.S. Pat. No. 6,623,785 on Sep. 23, 2003. The contents of the above identified applications and patent are incorporated by reference.

BACKGROUND

1. Field of the Invention

Present invention relates to apparatus and method for manufacturing pharmaceutical doses.

2. Description of the Art

Pharmaceutical doses in tablet or liquid form are made by pharmaceutical companies in formulations of a predetermined quantity of pharmaceutical units in each dose. Such pharmaceutical doses are frequently available in different strengths, such as 50 mg, 100 mg, etc.

A doctor typically prescribes a pharmaceutical or medication for a patient. The doctor, when prescribing a particular medication and medication strength, typically takes into account the patient's age, weight, sex, strong versus weak health condition, available dosage types, and the severity of the patient's illness, disease, or condition. The prescription is filled by a pharmacist who provides the selected pharmaceutical or medication in the desired strength and pharmaceutical type.

Errors can occur in this process due, for example, to the pharmacist being unable to clearly read the doctor's written prescription. This could cause the pharmacist to inadvertently select the improper strength or the wrong pharmaceutical. It would be desirable to provide a pharmaceutical dispensing apparatus and method which minimizes the occurrence of these problems.

For certain illnesses or physical conditions, people frequently take multiple pharmaceuticals at different times of the day, often in different combinations at different time intervals. Such a process is prone to error by the user by selecting the incorrect pharmaceuticals, or taking the proper pharmaceuticals at the wrong times or in the wrong combination. It would be desirable to provide a pharmaceutical dispensing apparatus and method which simplifies the taking of pharmaceuticals, especially combinations of different pharmaceuticals by providing multiple pharmaceuticals of selected strengths in one dose or pill.

Previously, fluid jetting devices based on ink-jet printer technology have been used to dispense chemicals onto a substrate. Piezoelectric or thermal jet heads with one or more fluid reservoirs or chambers have been used to dispense a plurality of fluid drops of defined volume onto a medium or substrate. Typically, the fluid jetting heads dispense the same constant fluid volume.

It would be desirable to provide an apparatus and method for the custom dispensing of pharmaceutical to form pharmaceutical doses where each pharmaceutical dose contains one of more pharmaceuticals in a single tablet or liquid dose and where the type of pharmaceutical, and the quantity of the selected pharmaceutical may be easily varied to meet a specific prescription or to manufacture a specific pharmaceutical dose.

It would also be desirable to provide an apparatus and method which is capable of dispensing variably selectable quantities of pharmaceuticals to a pharmaceutical receiving medium, such as a tablet or a liquid vial. It would be also be desirable to provide an apparatus and method which is capable of dispensing multiple, different pharmaceuticals in varied, selected quantities to a single pharmaceutical receiving medium.

It would also be desirable to provide an apparatus and method which is automatically responsive to an input prescription or pharmaceutical quantity signal to dispense the prescribed quantity and type of pharmaceutical to a pharmaceutical medium.

It would also be desirable to provide an apparatus and method which is capable of dispensing multiple pharmaceuticals in separate stages to a medium, each separated by a barrier or sealing layer to isolate the different pharmaceuticals from each other in the medium as well as to provide an outer barrier layer to protect the pharmaceuticals in the medium.

It would also be desirable to provide an apparatus and method for dispensing pharmaceuticals which uses replaceable pharmaceutical reservoirs enabling different pharmaceuticals to be dispensed and re-supplied.

SUMMARY OF THE INVENTION

The present invention is a pharmaceutical dispensing apparatus and method which is capable of dispensing variable quantities of one or more pharmaceuticals onto a pharmaceutical receiving medium thereby enabling a pharmaceutical dose to be custom manufactured to the particular needs of a user.

In one aspect, the present invention is a method of manufacturing a pharmaceutical dose. The method comprises the steps of:

supplying one fluid pharmaceutical component in a reservoir;

providing a pharmaceutical receiving medium;

fluidically coupling the reservoir to a fluid drop generator; and activating the fluid drop generator to eject a variably selected quantity of the one pharmaceutical component onto the pharmaceutical receiving medium.

The present method also includes the step of supplying the pharmaceutical component including the step of providing the one pharmaceutical component in a replaceable reservoir fluidically coupled to the fluid drop generator.

In another aspect of the invention, the step of supplying the pharmaceutical component further comprises the step of providing a plurality of pharmaceutical components each in a separate reservoir, each reservoir fluidically coupled to a different one of a plurality of fluid drop generators.

The method also includes the step of providing pharmaceutical component identification data to the controller for each reservoir connected to the fluid drop generators.

In another aspect, the method includes the step of controlling the activation of the fluid dispenser to dispense a variably selectable quantity of the one pharmaceutical component through the fluid drop generator to the pharmaceutical receiving medium.

In yet another aspect, the method includes the step of dispensing a barrier component onto the pharmaceutical receiving medium to seal a prior dispensed pharmaceutical component on the pharmaceutical receiving medium.

In yet another aspect of the present method, the method includes the step of providing a signal to the fluid dispenser from a remote signal source specifying a selected quantity of specified pharmaceutical component to be dispensed onto one pharmaceutical receiving medium. The signal from the remote source may also specify the selected quantities of a plurality of pharmaceutical components to be dispensed onto the one pharmaceutical receiving medium and patient information.

In yet another aspect of the invention, the method includes the steps of weighing the pharmaceutical receiving medium after the quantity of the pharmaceutical component or components have been dispensed onto the medium. The method compares the weight of the pharmaceutical receiving medium with a reference combined weight corresponding to the weight of an empty pharmaceutical receiving medium and the weight of the variably selected quantity of the one pharmaceutical component to verify that the selected quantity of the one pharmaceutical component which has been completely dispensed onto the medium.

In another aspect, the invention is an apparatus for manufacturing a pharmaceutical dose. The apparatus includes a reservoir containing one pharmaceutical component, a fluid drop generator fluidically coupled to the reservoir, and a control for activating the fluid drop generator to eject a variably selected quantity of the one pharmaceutical component onto the pharmaceutical receiving medium.

In this aspect of the invention, the supplying means is preferably a reservoir containing a single pharmaceutical component. Preferably, the reservoir is fluidically coupled to the fluid drop generator and replaceably mounted in the fluid dispenser.

In another aspect, the reservoir is a plurality of reservoirs, each containing a different pharmaceutical component. In this aspect, a plurality of fluid drop generators are provided in the fluid dispenser, with at least one fluid drop generator fluidically coupled to one of the plurality of reservoirs. Further, the plurality of reservoirs are preferably replaceably connected to the fluid dispenser.

In another aspect, the apparatus includes a communication means, coupled to the activating means or controller, for coupling a signal from a remote source carried on an external telecommunications network to the controller wherein the remote signal specifies the variably selectable quantity and/or the type of the one or more pharmaceutical components to be dispensed.

The apparatus also includes an optional weight detector for detecting and outputting signals corresponding to the weight of the pharmaceutical receiving medium after the pharmaceutical component or components have been dispensed onto the medium. The activating means or controller compares the detected weight with a reference or standard weight corresponding to the desired weight of the medium which has received the complete specified pharmaceutical quantity. Any discrepancies can be used for corrective action or to reject the particular medium.

In another aspect, the invention is a replaceable cartridge for an apparatus used to manufacturer a pharmaceutical dose which includes a control receiving data indicative of the pharmaceutical dose and dispensing droplets onto a pharmaceutical receiving medium. The replaceable cartridge includes a reservoir containing at least one pharmaceutical component and a fluid drop generator fluidically coupled to the reservoir. An information storage element may be provided on the replaceable cartridge for providing information concerning at least one parameter of the reservoir, the pharmaceutical dose or the state operative of the fluid drop generator.

In another aspect, the invention is a method of generating a custom pharmaceutical dose using a fluid drop generator operated by a controller to eject droplets of a pharmaceutical component from a reservoir onto a pharmaceutical receiving medium. The method includes the steps of providing information to the controller indicative of a particular prescription, and selecting a number of drops from a pharmaceutical component to be ejected from the reservoir through the fluid drop generator in response to the information.

This method envisions the selection of one or more of a plurality of fluid drop generators, each ejecting a different pharmaceutical component. The method also includes steps selecting the fluid drop generators in a plurality of different sequences or firing orders for dispensing a plurality of different pharmaceutical components.

The pharmaceutical dispensing apparatus and method of the present invention has numerous advantages compared to previous apparatus and methods for manufacturing pharmaceutical dosages, whether in tablet or liquid container form. The present apparatus and method uniquely enable a single pharmaceutical receiving medium, such as a tablet, to be manufactured with variably selected quantities of one or more pharmaceuticals. This enables a doctor or other prescription prescriber, as well as a manufacturer of mass distribution pharmaceutical doses, to custom make a pharmaceutical dose which meets the specific requirements of a particular user or at a particular strength, taking into account various user characteristics, such as age, weight, sex, general health condition, degree of illness, physical condition, etc. The pharmaceutical manufacturer may also be able to use the present apparatus and method to construct a plurality of pharmaceutical doses to suit a wide range of personal characteristics.

In addition, the present apparatus and method may be used to custom manufacture a single pharmaceutical dose in a single pharmaceutical receiving medium which contains multiple pharmaceuticals. This is ideally suited for users who take multiple pharmaceutical doses or pills in different combinations and at different times during each 24 hour period. The multiple pills or doses can be replaced with a single dose which contains all of the pharmaceuticals the user is to take at a specific time. This can minimize taking the wrong pharmaceutical dose, or missing some of the doses a user is supposed to take at a particular time.

The present method and apparatus are also connectable to an external telecommunication network to enable prescription order signals from a prescription prescriber, such as a doctor, to be transmitted, such as to the pharmaceutical manufacturing site. The specified quantities of the pharmaceutical or pharmaceuticals which a particular user is to take can be sent directly from the prescriber or doctor to the manufacturing site enabling the prescribed pharmaceuticals to be automatically dispensed into a medium or tablet. This minimizes the potential for error in interpreting the prescriber's instructions as well as minimizing error in the actual selection of the required quantity and type of each pharmaceutical.

The present apparatus and method also enables a cartridge carrying fluidically coupled reservoirs and fluid drop generators carrying different pharmaceuticals to be replaceably mounted in the dispensing apparatus. This enables a pharmacy to use the present apparatus and method to create many different pharmaceutical doses, simply by replacing one cartridge with a different cartridge containing a different pharmaceutical(s).

The present apparatus and method may also be employed by a pharmacy to manufacture a single type of pharmaceutical dose where the entire apparatus is replaced with a new apparatus containing new quantities of the required pharmaceutical or pharmaceuticals.

In the case of multiple pharmaceuticals injected into a single medium, the present apparatus and method may also be used to dispense a barrier or seal component which forms a seal layer between the different pharmaceuticals in a single pharmaceutical receiving medium. This prevents interaction between the pharmaceuticals before the medium is ingested by a user.

BRIEF DESCRIPTION OF THE DRAWINGS

The various features, advantages, and other uses of the present invention will become more apparent by referring to the following detailed description and drawing in which.

DESCRIPTION OF THE PREFERRED EMBODIMENTS

The present invention is an apparatus and method for dispensing pharmaceuticals to a pharmaceutical medium for manufacturing a pharmaceutical dose for a patient or user. The apparatus and method make unique use of an automated liquid ejecting device, such as a fluid jet dispenser having at least one pharmaceutical supply in a reservoir or chamber and at least one, and preferably, a plurality of jet heads or droplet generators in an array, each head dispensing a fixed volume of fluid in individual droplets from the reservoir on each activation of the head or drop generator. This arrangement enables the quantity of pharmaceutical(s) to be varied from dose to dose thereby enabling custom doses to be more easily prepared to suit the needs of each specific patient.

Figure 1:
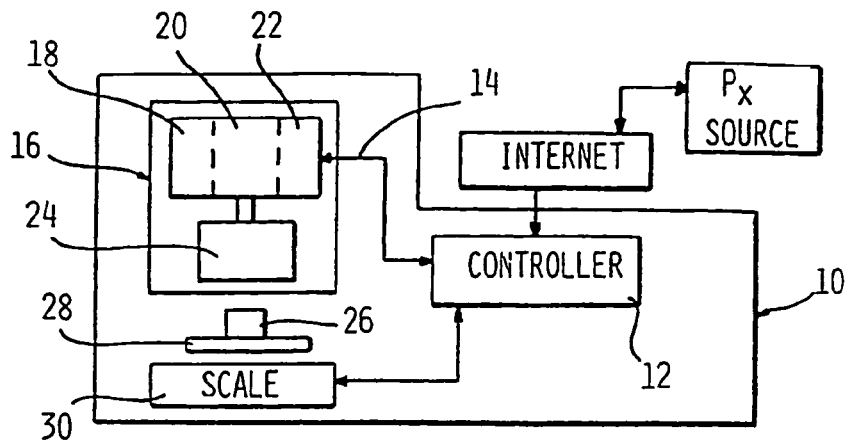
FIG. 1 is a block diagram of a pharmaceutical dispensing apparatus utilizing the method of the present invention.
Figure 2:
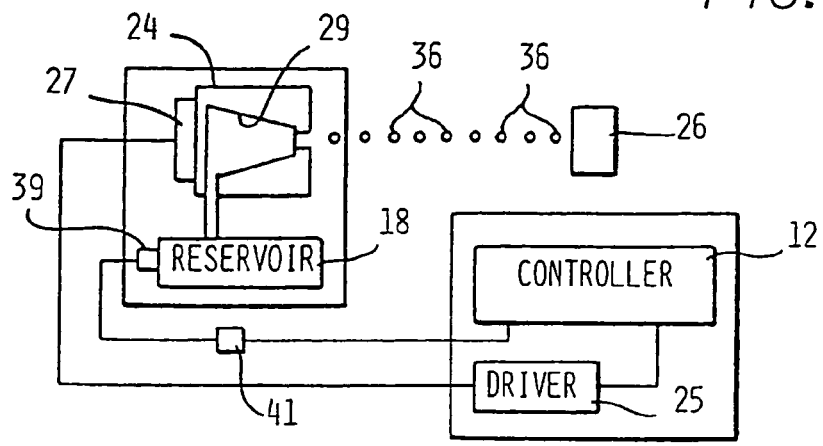
FIG. 2 is a pictorial representation of a fluid dispenser according to the present apparatus.

Referring now to the drawings, and to FIGS. 1 and 2 in particular, there is depicted a pharmaceutical dispensing apparatus 10 constructed in accordance with one aspect of the present invention. The apparatus 10 is depicted as a stand-alone apparatus which may be used in a pharmacy or other pharmaceutical dispensing location to automatically prepare custom pharmaceutical doses in response to prescription orders.

For the purposes of this description and the present invention, the term "pharmaceutical" is meant to include any type of drug, medication, chemical, or compound which is designed to be taken by a human as a medication to combat an illness or disease or to promote general health. Thus, pharmaceuticals as used herein, can be any drug, vitamin, or other chemical or compound which is used for health related purposes.

The apparatus 10 includes an activating means, such as a controller or control 12, which may be a computer or central processing unit based device operating a control program stored in a memory, not shown. The controller 12 provides output signals 14 to a fluid dispenser 16, such as a fluid-jet based device. Such a fluid dispenser, which may incorporate control and structural features of Hewlett-Packard Ink-Jet printer, Model Nos. HP-C1823D and HP51645A, for example, includes at least one reservoir 18 which contains a quantity of a specific type of one pharmaceutical. By way of example only, multiple reservoirs 20 and 22 are also provided in the fluid dispenser 16. Each reservoir 18, 20 and 22 may contain the same or different pharmaceutical. Alternately, a single reservoir can contain a plurality of separate compartments.

As is well known, such fluid dispenser 16 include at least one fluid drop generator or jetting head for each reservoir 18, 20, and 22. Preferably, an array 24 is provided with a plurality of heads or droplet generators divided into subgroups, with each subgroup containing a plurality of heads associated with one specific reservoir 18, 20, or 22.

The fluid dispenser 16 is a drop on demand type fluid dispenser, with piezoelectric or thermal fluid drop generators being preferred. FIG. 2 depicts a block diagram of a typical piezoelectric fluid drop generator 24 which is capable of dispensing individual droplets 36 upon each activation of a driver 25.

The piezoelectric driver 25 operating under control signals from the controller 12 supplies activating signals to a disk or layer of piezoelectric material 27 which is mechanically connected to a chamber 29 in one jetting head 24. The chamber 29 is disposed in fluid communication with one of the reservoirs, such as reservoir 18, whereby capillary action supplies fluid pharmaceutical from the reservoir 18 to the chamber 29. Upon each activation of the driver 25, the piezoelectric material 27 undergoes stress which results in mechanical movement of the piezoelectric material or element 27 resulting in a pumping action within the chamber 29 which expels individual droplets 36 through an orifice or outlet 33 in the jetting head 24.

It is preferred that each jetting head 24 be formed of materials that are inert to the pharmaceuticals which are to be dispensed therefrom. Thus, the jetting head 24 can be formed of inert materials, such as glass, ceramic, porcelain, inert plastic, etc.

The control signals 14 generated by the controller 12 control the selection of the heads or droplet generators 24 connected to a particular reservoir 18, 20, and 22 for each dispensing operation, which may include a plurality of fluid drops dispensed by the array of heads 24 connected to the selected reservoir or reservoirs 18, 20 or 22. Thus, the pictorial representation of a single jetting head 24 in FIG. 2 will be understood to represent all of the jetting heads 24 which form the array 24 of jetting heads in the fluid dispenser 16 of the present invention. Various combinations of jetting heads 24 and reservoirs 18, 20 and 22 may be utilized. For example, a single jetting head 24 may be associated with a single reservoir 18, 20 or 22. Alternately, a plurality of identical jetting heads 24 may be disposed in fluid communication with a single reservoir 18, 20 and 22, with similar groups of jetting heads 24 disposed in fluid communication with other reservoirs 18, 20 and 22.

The controller 12 is also capable of generating the control signals 14 which simultaneously or consecutively control the number of drops dispensed by each subgroup of heads 24 associated with one or more reservoirs, 18, 20, or 22. This enables, for example, multiple different pharmaceuticals to be dispensed onto a single pharmaceutical receiving medium 26.

The jetting heads 24, whether provided as a single jetting head 24 for each reservoir 18, 20 or 22 or as a plurality of groups of heads 24 for one or more reservoirs 18, 20 or 22, may be arranged in any particular spatial arrangement consistent with the shape of the pharmaceutical receiving medium 26, depending upon the manner in which the various pharmaceuticals are to be dispensed onto the medium 26, the speed of operation of the dispensing apparatus 10, etc. Thus, in one aspect, all of the jetting heads 24 in the array may be disposed in a single line. Alternately, various matrices of heads 24 may be provided for each particular reservoir 18, 20 and 22. The controller 12 may activate the head or heads 24 associated with one reservoir 18, 20 and 22 at a single time to dispense the complete variably selected quantity of the pharmaceutical from the single one reservoir 18, 20 or 22. If an additional pharmaceutical is to be added to the medium 26, the controller 12 will then activate the jetting heads 24 associated with a second one of the reservoirs 18, 20 and 22 to dispense the second pharmaceutical. Alternately, the controller 12 may send control signals to the jetting heads 24 associated with two or more of the reservoirs 18, 20 or 22 to simultaneously dispense all of the different pharmaceuticals which are selected for dispensing to the single medium 26. Further details of a preferred sequence of dispensing of one or more pharmaceuticals is discussed hereafter.

Although the number of heads 24 in each subgroup of heads associated with one particular reservoir 18, 20, and 22 typically have the same cross section or diameter so as to be able to eject the same known, constant volume of fluid upon each activation, it is possible in the present apparatus 10 to provide the heads 21 in at least one subgroup of heads 24 with a different diameter, either larger or smaller than the diameter of the heads 24 connected to other reservoirs 24 so as to dispense smaller or larger volumes of the pharmaceutical in the associated reservoir 18, 20, or 22 upon each activation of the fluid drop generator(s) 16.

The receiving medium 26 may be any suitable media used to receive, store, and transport pharmaceuticals. A porous sugar tablet or even a liquid receiving vial may be employed as the medium 26.

Since multiple pharmaceuticals are typically taken by a user over the course of an illness or within a short time period, multiple identical pharmaceutical filled mediums 26 can be formed by the apparatus 10 with the same selected quantity and type of pharmaceuticals. A media carrier 28, such as a conveyor, not shown, may be employed to advance new, unfilled media 26 into proximity with the jetting head array 24 as well as moving pharmaceutical filled media 26 away from the jetting head array 24 and to a packaging or unload station, not shown. For example, the entire fluid dispenser 16 may be mounted on a movable carriage, which is traversable in one or more directions with respect to the receiving medium 26 so as to bring the head array 24 into proximity with successive receiving mediums 26.

A weight detector 30 is shown in FIG. 1 as an optional part of the apparatus 10. The weight detector 30 may be any type of weighing device, such as an electronic scale, which is capable of measuring the weight of each receiving medium 26, both in an unfilled state and in a filled state. The output signals of the weight detector 30 are input to the controller 12. The controller 12 compares the measured weight of each filled medium 26 with a pre-stored, established reference or standard weight of a medium 26 and a complete quantity of a selected pharmaceutical to determine that the proper amount of pharmaceutical components have been dispensed to the medium 26.

The controller 12 can thus determine whether or not each medium 26 has been filled with the complete quantity of the selected pharmaceutical. If the detected weight comparison indicates that the medium 26 is too heavy, thereby indicating that too much pharmaceutical has been added to the medium 26, the controller 12 can activate a suitable reject apparatus, not shown, to reject the particular medium 26. Alternately, if the detected weight of the filled medium 26 is less than the standard or reference weight, the controller 12 can also generate signals activating the reject apparatus or, using feedback, determine the difference between the standard weight and measured weight of the medium 26 and then re-activate the heads 24 to dispense a selected amount of the pharmaceutical(s) to bring the weight difference to zero.

It should be noted that the cartridges 16 containing the reservoirs 18, 20, and 22 and heads 24 may be provided in different configurations, such as a single stand-alone, generally permanently attached cartridge 16 or as a replaceable cartridge 16. The single stand-alone configuration is suitable for a single use of the apparatus 10 where the reservoir or reservoirs 18, 20, and 22 are fully charged with pharmaceutical components by the pharmaceutical manufacturer, for example, and then shipped to the dispensing location, such as a pharmacy. When the pharmaceuticals in the reservoirs 18, 20, and 22 are exhausted, the apparatus 10 is exchanged for a completely new apparatus 10.

The apparatus 10 may also be constructed with replaceable cartridges 16. This provides the pharmacy with the ability to resupply pharmaceuticals when the existing supply of pharmaceutical components in any of the reservoirs 18, 20, and 22 is exhausted. At the same time, one or more cartridges 16 can be replaced with a different cartridge 16 containing a different pharmaceutical to prepare a different pharmaceutical dose.

Each of the plurality of reservoirs 18, 20, and 22 may be formed as separate, discrete reservoirs, each fluidically coupled to a head 24. Alternately, a single reservoir 18, 20, or 22 may contain individual, separate compartments defining the separate reservoirs 18, 20, and 22 for different pharmaceuticals.

FIG. 2 also depicts a data or information storage device 39 which may be associated with each of the reservoirs 18, 20 and 22, with only reservoir 18 being shown. The storage device 39 is any type of memory device suitable for storing and outputting information related to parameters of the pharmaceutical contained within the particular reservoir 18 and/or the reservoir itself. This is advantageously used with the standalone, non-replaceable combination of the reservoirs 18, 20 and 22 or the replaceable configuration reservoirs 18, 20 and 22. The storage device 39 may be a memory chip mounted on the reservoir 18 and connected to external contacts which mate with contacts in a connector 41 when the reservoir 18 is mounted in the fluid dispenser 16 and connected electrically or optically with the controller 12. Once the connection between the contacts on the storage device 39 and the connector 41 is made, the controller 12 is disposed in electrical communication with the storage device 39 for information transfer with the storage device 39.

The data in the information storage device 39 can be in the form of a code identifying the particular pharmaceutical component contained in the reservoir, such as a bar code, etc., which can be read by any suitable reader, including a laser optical reader. Alternately, electrical contacts or other signal generating devices can be carried on each storage device 39 to provide a code output which can be read by a code reader in the connector 41 or in the controller 12.

The information in the storage device 39 may be such as to enable the controller 12 to digitally determine the type of pharmaceutical in the reservoir 18 as well as other information, such as the quantity of the pharmaceutical remaining in the reservoir 18 based on the number of drops dispensed or the number of times that the jetting head(s) 24 coupled to the particular reservoir 18 has been activated. Other parameters which can be stored in the storage device 39 include a date code of manufacture of the pharmaceutical, an inspection date, system coefficients, reservoir size, age of the pharmaceutical, to name just a few.

The controller 12 can thereby verify that the proper pharmaceutical component is provided in the appropriate reservoir location or merely identify which pharmaceutical component is present. An example of a fluid dispenser having retrievable reservoir identification information is described in U.S. Pat. No. 6,039,430, assigned to the Assignee of the present invention. The entire contents of this patent are incorporated herein.

Another aspect of the present invention is also shown in FIG. 1 wherein an electrical communication device is provided in the controller 12 or as a separate element electrically connected to the controller 12. The receiver is coupled to a telecommunication network by various means including hard conductors, cables, wireless transmission, etc. The telecommunication network may thus comprise an existing telephone communication network, as well as a wireless radio frequency network, cellular telephone network, satellite communication network, the Internet, etc.

In the case of a wireless communication network, the receiver is coupled to an antenna for receiving signals from a remote signal source, such as a doctor's office or other prescription issuing authority. These signals contain, for example, patient identifying data, as well as the type(s) of pharmaceuticals, the quantity in terms of the number of dosage units to be made, the dosage strength, etc. These signals are input to the controller 12 which then activates the fluid dispenser 16 in the appropriate manner to prepare the specified pharmaceutical doses. This automatic system has the advantage of minimizing errors in interpreting a doctor's handwritten prescription order as well as potential errors in manually filling the prescription.

At least a portion of the signals received by the receiver may be stored in the memory of the controller 12 for future use by the fluid dispenser 16. For example, signals specifying patient identification data, such as name, address, telephone number, authorized doctor, health insurance provider, etc., may be transmitted to or otherwise stored in the memory of the controller 12. This would enable, for example, the apparatus 10 to be used whenever a patient desires to refill a prescription. Remote signals via a telephone or computer network from the patient to the apparatus 10 may be employed to generate a new order. Alternately, the pharmacy may take a telephone call or face-to-face verbal instructions from a patient and then input appropriate signals to the controller 12 through push buttons or other input means, including computer inputs to fill a prescription for the patient.

Figure 5:
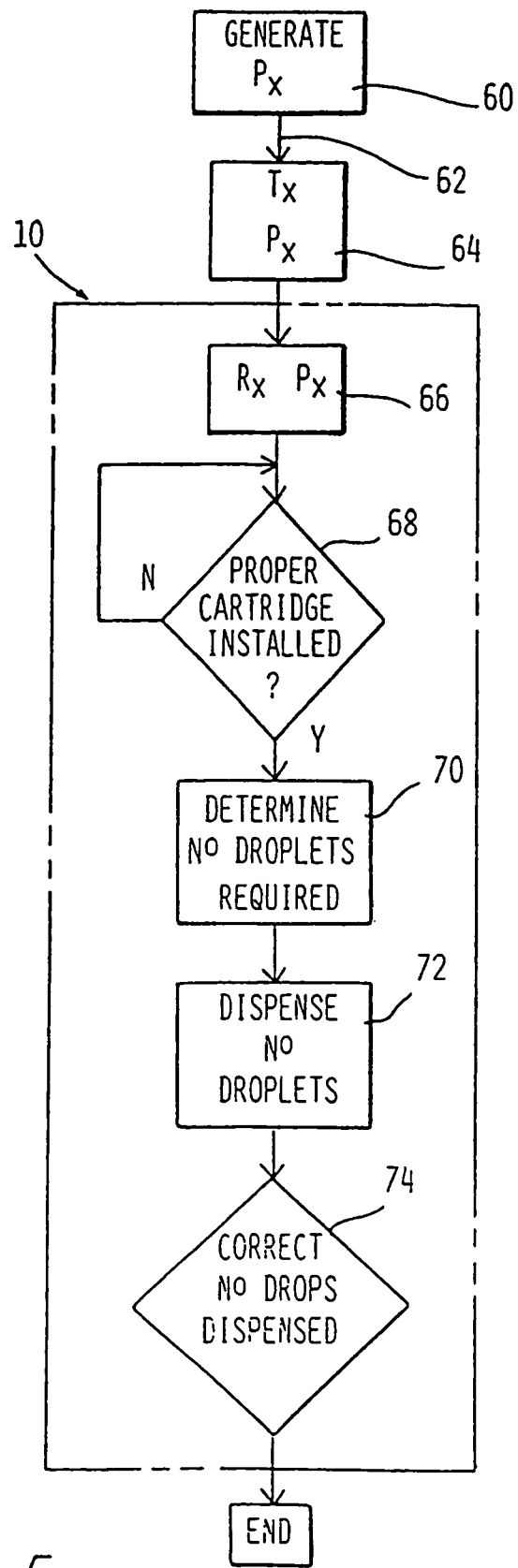
FIG. 5 is a flow diagram of the sequence of operation of the pharmaceutical dispensing apparatus and method of the invention.

An example of this communication sequence is shown in FIG. 5. In step 60, a prescription is generated by a doctor or other prescription generating source. This prescription is transmitted via a communication link 62 in step 64 from the prescription source to the controller 12 via any communication link described above. The prescription is received by a suitable signal receiving element or receiver coupled to the controller 12 in step 66. The controller 12 then stores the received prescription which specifies the type of pharmaceutical component(s) as well as the quantity of the pharmaceutical component(s) which are to be used in each pharmaceutical dose.

The controller 12 then determines in step 68 if a cartridge containing the required pharmaceutical component or components is installed in the fluid dispenser 16. Step 68 may include sub-steps in which a plurality of coupled reservoir and fluid drop generators are detected as being installed in the fluid dispenser 16.

In step 70, the controller 12 determines the number of drops of the selected pharmaceutical component(s) which are required for each pharmaceutical dose. In step 72, the controller 12 then generates signals to the cartridge 16 in the fluid dispenser 16 and, specifically, to the fluid drop generator to dispense the selected number of drops of each pharmaceutical component from the reservoir onto the pharmaceutical receiving medium 26.

Step 74 represents a determination made by the controller if the correct number of drops of pharmaceutical component(s) have been dispensed onto the medium 26. Step 24 can be implemented via the weighing means or scale 30 as well as an indication from the information storage element 36 on each reservoir and fluid drop generator which may contain information specifying the number of drop dispensing signals which have been received from the controller 12.

Figure 3A:
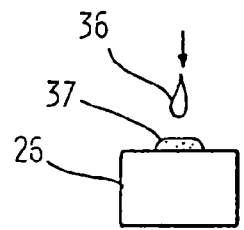
FIGS. 3A and 3B are pictorial representations of the sequential steps in the method of the present invention.
Figure 3B:
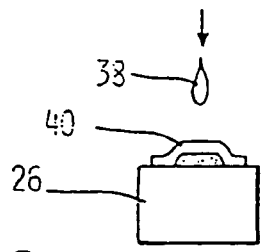

Referring now to FIGS. 3A and 3B, there is depicted a first method sequence according to the present invention. In this sequence, the fluid dispenser 16 is configured for dispensing a single pharmaceutical component onto each receiving medium 26, such as a tablet. In FIG. 3A, the head array 24 has been activated by the controller 12 to dispense one and, typically, a plurality of fluid drops 36 onto the medium 26. For clarity in understanding the invention, the fluid drop 36 of the single pharmaceutical is shown as being deposited on the surface of the receiving medium 26 in a layer 37. Although this is possible, typically the receiving medium 26 will be formed of a porous material which will allow the fluid pharmaceutical to be absorbed into the interior of the medium 26.

Next, a different subgroup of heads in the head array 24 are activated by the controller 12 to dispense droplets 38 from a different reservoir 18, 20, or 22, as shown in FIG. 2C, over the first dispensed pharmaceutical on the medium 26. This second component can be a barrier material, such as a clear coat or other inert material which will not interact with the first dispensed pharmaceutical component. The droplets 38 harden or dry to form a barrier layer 40 over the first dispensed droplets 36 and, possibly, over the entire exterior surface of the medium 26.

Figure 4A:
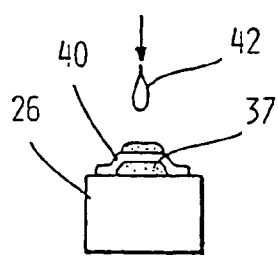
FIGS. 4A and 4B are pictorial representations of optional method steps according to the present invention.
Figure 4B:
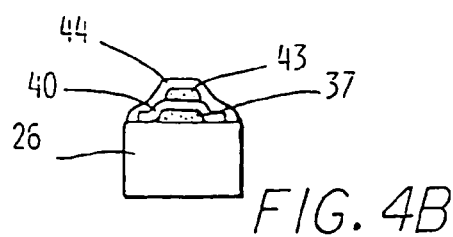

An optional method sequence is shown in FIGS. 4A and 4B. In this aspect of the present inventive method as shown in FIG. 4A, the pharmaceutical medium 26 has the first pharmaceutical component layer 37 and the barrier layer 40 deposited thereon as described above and shown in FIGS. 3A and 3B. Next, one or more drops 42 of a second pharmaceutical component, which can be different from the first pharmaceutical component in layer 37 are dispensed over the barrier layer 40 on the medium 26 in a layer 43. Next, an optional outermost barrier layer 44 is dispensed from one reservoir 18, 20, or 22 over the second pharmaceutical layer 43, and the initial barrier layer 40.

In summary, there has been disclosed a unique pharmaceutical dispensing apparatus and method which enables pharmaceuticals in tablet, or liquid form to be custom manufactured in different strengths or quantities or in multiple combinations in a single dose to suit the specific requirements of an individual user. Further, the apparatus and method can utilize communication signals between a pharmaceutical ordering location, such as a doctors office, and the pharmaceutical manufacturing location, to automatically generate each prescribed pharmaceutical thereby minimizing potential human errors in interpreting a prescription order and properly filling the prescription order.

What is claimed is:

1. An apparatus for manufacturing a variably selected pharmaceutical and dose on a succession of pharmaceutical dosage forms, the apparatus comprising:

at least one reservoir containing at least one fluid pharmaceutical component;

a fluid drop generator fluidically coupled to the at least one reservoir, the fluid drop generator including at least one array of jetting heads variably sized with different head diameters; and a control activating the fluid drop generator, the fluid drop generator configured to eject variably selected individual droplets of variable number and size of the at least one pharmaceutical component onto the dosage form;

wherein the fluid drop generator is mounted on a moveable carriage configured to be traversable in at least one direction with respect to the dosage forms so that the at least one array of jetting heads is simultaneously in a position to apply the variably selected pharmaceutical and dose onto the succession of pharmaceutical dosage forms;

and wherein the fluid drop generator is a drop on demand fluid dispenser selected from the group consisting of a thermal inkjet drop generator and a piezoelectric inkjet drop generator.

2. The apparatus of claim 1 wherein the reservoir comprises a plurality of reservoirs, each containing a different pharmaceutical component.

3. The apparatus of claim 2 wherein the fluid dispenser comprises a plurality of fluid drop generators, at least one separate one of the plurality of fluid drop generators connected to one of the plurality of reservoirs.

4. The apparatus of claim 1, further comprising a signal communication receiver coupled to the control and an external telecommunications network, the communication receiver communicating a signal from a remote signal source specifying the variably selectable quantity of the at least one pharmaceutical component to the control.

5. The apparatus of claim 1, further comprising a weight detector for detecting and outputting signals corresponding to the weight of the pharmaceutical dosage form after the at least one pharmaceutical component has been dispensed onto the pharmaceutical dosage form.

6. The apparatus of claim 1 wherein the one reservoir comprises a single reservoir including a plurality of separate compartments, each compartment containing a different pharmaceutical component.

7. The apparatus of claim 1, further comprising an information storage element carried on the reservoir and the fluid drop generator, the information storage element electrically connectable to the control and providing communicatable information to the control of at least one parameter of the at least one pharmaceutical component and the fluid drop generator.

8. The apparatus of claim 1 wherein the pharmaceutical dosage form is ingestible.

9. A replaceable cartridge in an apparatus for manufacturing a variably selected pharmaceutical and dose on a succession of pharmaceutical dosage forms, the apparatus including a control receiving data indicative of the pharmaceutical and dose and dispensing droplets of at least one pharmaceutical component onto a succession of pharmaceutical dosage forms, the replaceable cartridge comprising:

at least one reservoir containing at least one pharmaceutical component; and a fluid drop generator fluidically coupled to the at least one reservoir and configured to dispense variably selected individual droplets of variable number and size from the at least one reservoir to the pharmaceutical dosage form, the fluid drop generator including at least one array of jetting heads variably sized with different head diameters;

wherein the fluid drop generator is mounted on a moveable carriage configured to be traversable in at least one direction with respect to the dosage forms so that the at least one array of jetting heads is simultaneously in a position to apply the variably selected pharmaceutical and dose onto the succession of pharmaceutical dosage forms;

and wherein the fluid drop generator is a drop on demand fluid dispenser selected from the group consisting of a thermal inkjet drop generator and a piezoelectric inkjet drop generator.

10. The replaceable cartridge of claim 9, further comprising:

an information storage element carried on the reservoir and the fluid drop generator, the information storage element electrically connectable to the control and providing communicatable information to the control of at least one parameter of the pharmaceutical component and the fluid drop generator.

11. The replaceable cartridge of claim 10 wherein the fluid drop generator is integrally coupled to the reservoir.

12. The replaceable cartridge of claim 11 wherein the information storage element contains information specifying the number of drops to be dispensed by the fluid drop generator.

13. The replaceable cartridge of claim 9 wherein the fluid drop generator is integrally coupled to the reservoir.

14. The replaceable cartridge of claim 9 wherein the reservoir is a single reservoir including a plurality of separate compartments, each containing one pharmaceutical component.

15. The replaceable cartridge of claim 9 wherein the pharmaceutical dosage form is ingestible.

16. An apparatus for manufacturing a variably selected pharmaceutical and dose on a succession of pharmaceutical dosage forms, the apparatus comprising:

an integral replaceable unit, including:
at least one reservoir including a plurality of separate compartments, each compartment containing a different pharmaceutical component;

a fluid drop generator fluidically coupled to the at least one reservoir, the fluid drop generator including at least one array of jetting heads variably sized with different head diameters; and a control activating the fluid drop generator, the fluid drop generator configured to eject variably selected individual droplets of variable number and size of the different pharmaceutical components onto the dosage form;

wherein the fluid drop generator is mounted on a moveable carriage configured to be traversable in at least one direction with respect to the dosage forms so that the at least one array of jetting heads is simultaneously in a position to apply the variably selected pharmaceutical and dose onto the succession of pharmaceutical dosage forms;

and wherein the fluid drop generator is a drop on demand fluid dispenser selected from the group consisting of a thermal inkjet drop generator and a piezoelectric inkjet drop generator.

* * * * *

UNITED STATES PATENT AND TRADEMARK OFFICE
CERTIFICATE OF CORRECTION

PATENT NO. : 7,707,964 B2  Page 1 of 1
APPLICATION NO. : 11/361438
DATED : May 4, 2010
INVENTOR(S) : Winthrop D. Childers It is certified that error appears in the above-identified patent and that said Letters Patent is hereby corrected as shown below:

In column 12, lines 15-22, in Claim 10, delete
"10. The replaceable cartridge of claim 9, further comprising:
an information storage element carried on the reservoir and
the fluid drop generator, the information storage element
electrically connectable to the control and providing
communicatable information to the control of at least
one parameter of the pharmaceutical component and the
fluid drop generator." and insert
-- 10. The replaceable cartridge of claim 9, further comprising
an information storage element carried on the reservoir
and the fluid drop generator, the information storage element
electrically connectable to the control and providing communicatable
information to the control of at least one parameter of the at least one
pharmaceutical component and the fluid drop generator. --, therefor.

Signed and Sealed this

Thirty-first Day of August, 2010

David J. Kappos
*Director of the United States Patent and Trademark Office*